United States Patent [19]

Sekine et al.

[11] Patent Number: 5,753,672

[45] Date of Patent: May 19, 1998

[54] IMIDAZOPYRIDINE DERIVATIVES AND PROCESS FOR PREPARING THE SAME

[75] Inventors: Yasuo Sekine, Kawaguchi; Eiji Kawanishi, Kitamoto; Hiroshi Narita; Yoshihiro Hashimoto, both of Urawa; Masakazu Mizobe, Takatsuki, all of Japan

[73] Assignee: Tanabe Seiyaku Co., Ltd., Osaka, Japan

[21] Appl. No.: 871,540

[22] Filed: Jun. 9, 1997

Related U.S. Application Data

[63] Continuation-in-part of Ser. No. 415,568, Apr. 3, 1995, abandoned.

[30] Foreign Application Priority Data

Apr. 19, 1994 [JP] Japan .................. 6-079079

[51] Int. Cl.$^6$ .................. A61K 31/44; C07D 471/04
[52] U.S. Cl. .................. 514/303; 546/118
[58] Field of Search .................. 546/118; 574/303

[56] References Cited

U.S. PATENT DOCUMENTS

| 5,091,390 | 2/1992 | Ardecky et al. | 514/303 |
| 5,409,936 | 4/1995 | Honma et al. | 514/303 |
| 5,424,316 | 6/1995 | Honma et al. | 514/303 |

FOREIGN PATENT DOCUMENTS

| A78201 | 12/1991 | Australia . |
| 0245637 | 11/1987 | European Pat. Off. . |
| 0253310 | 1/1988 | European Pat. Off. . |
| 0291969 | 11/1988 | European Pat. Off. . |
| 0399731 | 11/1990 | European Pat. Off. . |
| 0400835 | 12/1990 | European Pat. Off. . |
| 0420237 | 4/1991 | European Pat. Off. . |
| 0425921 | 5/1991 | European Pat. Off. . |
| 0434038 | 6/1991 | European Pat. Off. . |
| 0461039 | 12/1991 | European Pat. Off. . |
| 0468470 | 1/1992 | European Pat. Off. . |
| 0531874 | 3/1993 | European Pat. Off. . |
| 0546358 | 6/1993 | European Pat. Off. . |

OTHER PUBLICATIONS

Blankley et al., *J. Med. Chem.*, vol. 34, No. 11, pp. 3248–3260, Nov., 1991.
Klutchko et al., *Journal of Heterocyclic Chemistry*, vol. 28, No. 1, pp. 97–108, Jan., 1991.
Bundgaard H in "Design of Prodrugs" (1985) Elsevier. Amsterdam –New York –Oxford. pp. 4–5.
Bodin No. Ekstrom B. Forsgren U. Jalar L. Magni L. Ramsay CH. Sjoberg B. (1975) Antimicrob. Agents Chemotherapy. 8, 518–525.

Primary Examiner—C. Warren Ivy
Assistant Examiner—Evelyn Huang
Attorney, Agent, or Firm—Birch, Stewart, Kolasch & Birch, LLP

[57] ABSTRACT

An imidazopyridine derivative of the formula [I]:

wherein $R^1$ is a lower alkyl group, $R^2$ is a lower alkanoyl group, and $R^3$ and $R^4$ are each lower alkyl groups, or both combine at the end thereof to form an alkylene group having 3 to 6 carbon atoms, and a pharmaceutically acceptable salt thereof, said imidazopyridine derivatives have an excellent angiotensin II antagonistic activity and are useful for the prophylaxis or treatment of hypertension.

7 Claims, No Drawings

IMIDAZOPYRIDINE DERIVATIVES AND PROCESS FOR PREPARING THE SAME

This application is a continuation-in-part of application Ser. No. 08/415,568 filed on Apr. 3, 1995, now abandoned.

The present invention relates to novel imidazopyridine derivatives having a hypotensive activity, and a process for preparing the same.

PRIOR ART

Angiotensin II is a biologically active peptide consisting of eight amino acids, which is produced by specific conversion of angiotensin I by an angiotensin converting enzyme mainly during the circulation in the lung. Said angiotensin II constricts the vascular smooth muscle as well as promotes the secretion of aldosterone in the adrenal cortex, by which the blood pressure is increased. Therefore, it is well known that angiotensin II receptor antagonists may be useful in the treatment of hypertension.

Based on the above-mentioned mechanism, there have been known some hypotensive agents, for example, imidazopyridine derivatives such as 2-(lower alkyl)-5-(lower alkanoyl)-3-(substituted biphenylyl)methyl-4,5,6,7-tetrahydroimidazo[4,5-c]pyridine-4-carboxylic acids, and a pharmaceutically acceptable salt thereof (cf. Japanese Patent First Publication (Kokai) No. 279361/1993).

Said known compounds have some problems when used clinically. For example, some compounds have difficulty in being absorbed from the digestive organs when administered orally, or even if being absorbed well at the digestive organs, other compounds are hardly converted into the active form in the plasma after being absorbed.

Under the above-mentioned circumstances, it has been desired to develop a compound which can be well absorbed from the digestive organs and thereafter, becomes quickly the active form in the plasma so that it can show excellent pharmacological activities.

BRIEF DESCRIPTION OF THE INVENTION

An object of the present invention is to provide novel imidazopyridine derivatives which can be well absorbed from the digestive organs and quickly become the active form, by which they show a potent angiotensin II antagonistic activity so that they are useful as hypotensive agents. Another object of the present invention is to provide a process for preparing said imidazopyridine derivatives. A further object of the present invention is to provide a pharmaceutical composition comprising as an active ingredient the novel imidazopyridine derivative or a pharmaceutically acceptable salt thereof in admixture with a conventional pharmaceutically acceptable carrier or diluent. A still further object of the present invention is to provide a method of prophylaxis or treatment of hypertension in warm-blooded animals including human beings.

DETAILED DESCRIPTION OF THE INVENTION

The present invention relates to imidazopyridine derivatives of the formula [I]:

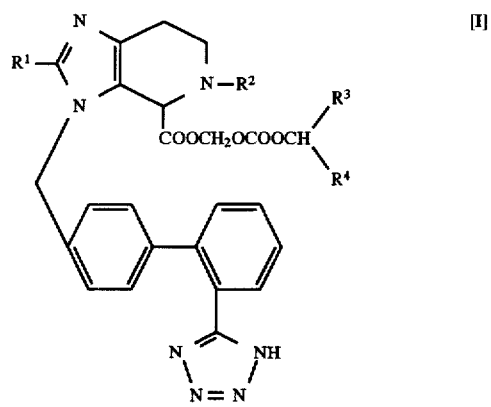

wherein $R^1$ is a lower alkyl group, $R^2$ is a lower alkanoyl group, and $R^3$ and $R^4$ are each lower alkyl groups, or both combine at the end thereof to form an alkylene group having 3 to 6 carbon atoms, or a pharmaceutically acceptable salt thereof.

Preferred examples of the present compounds [I] are 2-n-propyl-5-acetyl-3-[2'-(1H-tetrazol-5-yl)biphenyl-4-yl]methyl-4,5,6,7-tetrahydroimidazo[4,5-c]pyridine-4-carboxylic acid (3-pentyl)oxycarbonyloxymethyl ester, 2-n-propyl-5-acetyl-3-[2'-(1H-tetrazol-5-yl)biphenyl-4-yl]methyl-4,5,6,7-tetrahydroimidazo[4,5-c]pyridine-4-carboxylic acid cyclohexyloxycarbonyloxymethyl ester, and the like.

The present compounds [I] and their pharmaceutically acceptable salt thereof are useful as a medicament for the prophylaxis or treatment of hypertension in human beings or other warm-blooded animals.

The present compounds [I] may be used as a medicament either in the free form or a pharmaceutically acceptable salt thereof. The pharmaceutically acceptable salt is preferably a hydrochloride thereof, which shows an excellent crystallizability.

The present compounds [I] may exist in the form of an optically isomer due to an asymmetric carbon atom thereof, and the present invention also includes these optically active isomers and a mixture thereof.

The present compounds [I] or a pharmaceutically acceptable salt thereof is suitable for an oral administration, but can be used for a parenteral administration. The present compounds [I] or a pharmaceutically acceptable salt thereof may also be used in the form of a pharmaceutical preparation in admixture with a pharmaceutically acceptable carrier or diluent being suitable for oral administration or parenteral administration. The pharmaceutical preparations may be in a solid form such as tablets, capsules, powders, etc., or in a liquid form such as solutions, suspensions, emulsions, etc. When administered parenterally, the present compounds [I] or a pharmaceutically acceptable salt thereof may be used in the form of an injection preparation.

The daily dose of the present compounds [I] or a pharmaceutically acceptable salt thereof varies depending on age, weight, conditions of patients and severity of diseases, but when administered orally, it is usually in the range of 0.01 to 30 mg/kg, preferably in the range of 0.03 to 5 mg/kg, and when administered parenterally, it is usually in the range of 0.002 to 1 mg/kg, preferably in the range of 0.01 to 0.3 mg/kg.

According to the present invention, the present compounds [I] may be prepared by reacting a compound of the formula [II]:

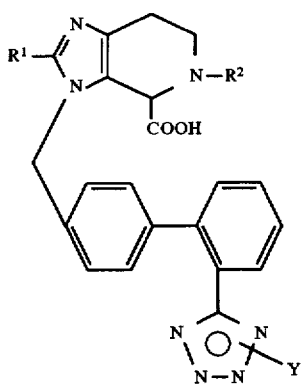

[II]

wherein Y is a hydrogen atom or a protecting group, and $R^1$ and $R^2$ are the same as defined above, or a salt thereof, or a reactive derivative at the carboxyl group thereof, with a compound of the formula [III]:

[III]

wherein X is a reactive residue, and $R^3$ and $R^4$ are the same as defined above, and when Y is a protecting group, followed by removing said protecting group from the product.

The reaction of the compound [II], or a salt thereof, or a reactive derivative at the carboxyl group thereof, with the compound [III] may be carried out by a conventional method.

The salt of the compound [II] is, for example, an alkali metal salt, an alkaline earth metal salt, an organic amine salt, etc. The reactive derivative at the carboxyl group of the compound [II] is preferably a corresponding acid halide, acid anhydride, active ester, etc. The reactive residue represented by X in the compound [III] is preferably a halogen atom (e.g. chlorine, bromine, iodine, etc.).

For example, the reaction of the free compound [II] or a salt thereof with the compound [III] is carried out in the presence of an acid acceptor. The acid acceptor includes, for example, an alkali metal carbonate (e.g. potassium carbonate, etc.), an alkali metal hydride (e.g. sodium hydride, potassium hydride, etc.), an alkali metal alkoxide (e.g. sodium methoxide, sodium ethoxide, potassium t-butoxide, etc.), an organic amine (e.g. a trialkylamine, pyridine, etc.), an alkali metal hydrogen carbonate (e.g. sodium hydrogen carbonate, potassium hydrogen carbonate, etc.).

These reactions may preferably be carried out in a suitable solvent (e.g. an ether solvent such as dioxane, tetrahydrofuran, a di-lower alkyl formamide, a di-lower alkyl sulfoxide, acetone, methyl ethyl ketone, ethyl acetate, acetonitrile, chloroform, methylene chloride, etc.) at a temperature of from under cooling to with heating, e.g. at a temperature of from −30° C. to 100° C., preferably at a temperature of from −10° C. to room temperature.

When a product obtained in the above reactions has a protecting group, said protecting group may be easily removed by a conventional method. The protecting group is, for example, a trityl group, a tri-lower alkylsilyl group, a cyano-lower alkyl group, or a lower alkoxybenzyl group.

The present compounds [I] may also be prepared by reacting a compound of the formula [IV]:

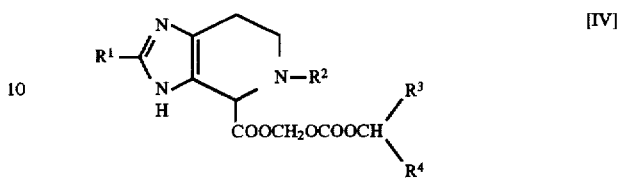

[IV]

wherein $R^1$, $R^2$, $R^3$ and $R^4$ are the same as defined above, or a salt thereof, with a compound of the formula [V]:

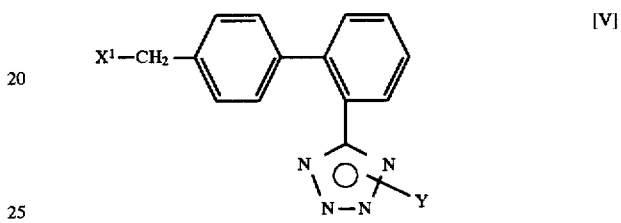

[V]

wherein $X^1$ is a reactive residue, and Y is the same as defined above, or a salt thereof, and when Y is a protecting group, followed by removing said protecting group from the product.

Further, the present compounds [I] may also be prepared by reacting a compound of the formula [VI]:

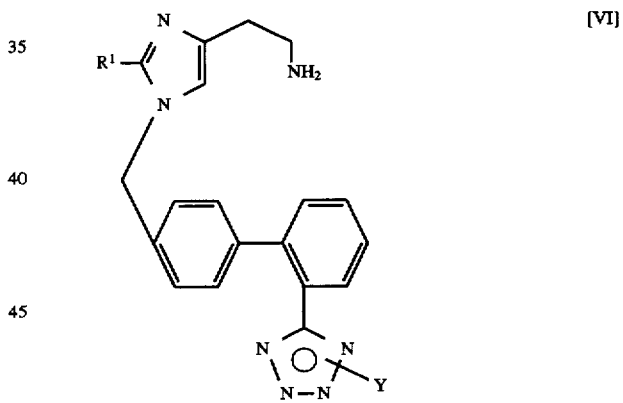

[VI]

wherein $R^1$ and Y are the same as defined above, or a salt thereof, with a compound of the formula [VII]:

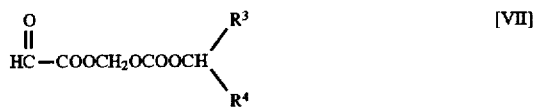

[VII]

wherein $R^3$ and $R^4$ are the same as defined above, to give a compound of the formula [VIII]:

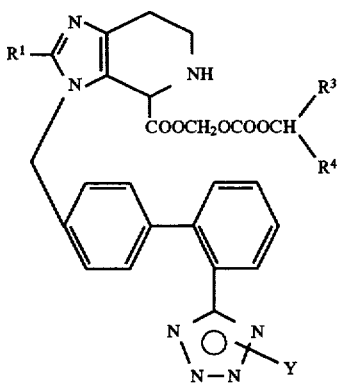

wherein $R^1$, $R^3$, $R^4$ and Y are the same as defined above, followed by reacting the compound [VIII] with a compound of the formula [IX]:

 [IX]

wherein $R^2$ is the same as defined above, or a salt thereof, or a reactive derivative thereof, and when Y is a protecting group, followed by removing said protecting group.

The reaction of the compound [IV] with the compound [V] may be carried out in the presence of an alkali metal hydride or an alkali metal alkoxide, or in the presence of an acid acceptor. The suitable example for the reactive residue represented by $X^1$ in the compound [V] is a halogen atom.

When the reaction is carried out in the presence of an alkali metal hydride or an alkali metal alkoxide, the alkali metal hydride includes, for example, sodium hydride, potassium hydride, etc., and the alkali metal alkoxide includes, for example, sodium methoxide, sodium ethoxide, potassium t-butoxide, etc. The reaction is preferably carried out in a suitable solvent at a temperature of from under cooling to with heating, for example, at a temperature of from −30° C. to 50° C., preferably at a temperature of from −10° C. to room temperature. The solvent includes, for example, a di-lower alkyl formamide, a di-lower alkyl sulfoxide, a di-lower alkyl acetamide, and a lower alkanol.

When the reaction is carried out in the presence of an acid acceptor, the acid acceptor includes, for example, an alkali metal carbonate, etc. The reaction is preferably carried out at a temperature of from under cooling to with heating, for example, at a temperature of from −10° C. to 100° C. The solvent is, for example, acetone, dimethyl formamide, dimethylsulfoxide, etc.

The present compounds [I] may be obtained in the form of a mixture of two stereoisomers, which are prepared by reacting the compound [V] with the compound [IV] at 1-position of the imidazopyridine nucleus or 3-position thereof. In this case, these isomers may be separated by a conventional method such as silica gel column chromatography, recrytallization, etc.

The reaction of the compound [VI] with the compound [VII] may be carried out in the presence or absence of an acid or base. When the reaction is carried out in the presence of an acid or base, the acid includes, for example, an inorganic acid (e.g. hydrochloric acid, sulfuric acid, phosphoric acid, etc.), and an organic acid (e.g. oxalic acid, fumaric acid, etc.), and the base includes, for example, an inorganic base such as an alkali metal carbonate, an alkali metal hydrogen carbonate, etc. The reaction is carried out in a suitable solvent at a temperature of from under cooling to with heating, for example, at a temperature of from 10° C. to 100° C., preferably at a temperature of from room temperature to a boiling point of the solvent to be used. The solvent includes, for example, water or a lower alkanol, or tetrahydrofuran, dioxane, or a mixture of these solvents and water.

The reaction of the compound [VIII], which is obtained by the reaction of the compound [VI] with the compound [VII], with the compound [IX] is carried out by a conventional method. For example, the reaction is carried out in the presence or absence of a base or dehydrating-condensing agent.

The compound [IX] may be used in the form of a reactive derivative, for example, in the form of an acid anhydride thereof, or an acid halide thereof.

When the reaction is carried out in the presence of a base, the base may be any conventional ones, preferably an organic base such as a tri-lower alkylamine, pyridine, a 4-di-(lower alkyl)aminopyridine, and an inorganic acid such as an alkali metal hydrogen carbonate, an alkali metal carbonate, an alkali metal hydroxide, etc. The reaction may be carried out in a suitable solvent at a temperature of from under cooling to with heating, for example, at a temperature of from −30° C. to 100° C., preferably at a temperature of from −10° C. to a boiling point of the solvent to be used. The solvent includes, for example, methylene chloride, chloroform, ethyl acetate, tetrahydrofuran, ether, or a mixture of these solvents and water.

When the reaction is carried out in the presence of a dehydrating-condensing agent, the dehydrating-condensing agent includes, for example, dicyclohexylcarbodiimide, 1-ethyl-3-(3-dimethylaminopropyl)carbodiimide, benzotriazol-1-yloxytris(dimethylamino)phosphonium hexafluorophosphate, etc. It may be added a reaction promoter such as hydroxybenzotriazole, N-hydroxysuccinimide, etc. to the reaction system. The reaction is carried out in a suitable solvent at a temperature of from under cooling to with heating, for example, at a temperature of from −10° C. to 80° C., preferably at around room temperature. The solvent includes, for example, methylene chloride, chloroform, a di-lower alkylformamide, acetonitrile, tetrahydrofuran, etc.

In the above-mentioned reactions, the starting compounds may be used either in the free form or in the form of a salt thereof. The salt of the compound [IV] may be, for example, hydrochloride, hydrobromide, oxalate, etc. The salt of the compound [V] may be, for example, an alkali metal salt, etc. The salt of the compound [VI] may be, for example, hydrochloride, hydrobromide, oxalate, etc. The salt of the compound [VIII] may be, for example, an alkali metal salt, an alkaline earth metal salt, a heavy metal salt, an organic amine salt, a salt with an inorganic acid, a salt with an organic acid, etc. The salt of the compound [IX] may be, for example, an alkali metal salt, an alkaline earth metal salt, etc. The compound [VII] may be used in the form of a hydrate thereof, an alcoholate thereof.

When the present compounds [I] thus obtained are in the form of a racemic mixture, said racemic compounds [I] may be optically resolved by a conventional method.

The starting compound [II] and the starting compound [VI] may be prepared according to the method disclosed in Japanese Patent First Publication (Kokai) No. 279361/1993.

The starting compound [IV] may be prepared according to the method disclosed in Japanese Patent First Publication (Kokai) No. 167687/1986 or 101062/1990.

The starting compound [III] may be prepared according to the method disclosed in Rep. Yamanouchi Cent. Res. Lab., No. 2, pp. 95 (1974). Among the starting compounds [III], the starting compound [III] in which X is a chlorine atom may also be prepared by reacting methyl chloroformate with sulfuryl chloride to give monochloromethyl chloroformate, followed by reacting monochloromethyl chloroformate with an alcohol compound of the formula [X]:

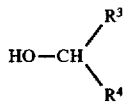

wherein $R^3$ and $R^4$ are the same as defined above.

In the present description and claims, the lower alkyl group means alkyl groups having 1 to 6 carbon atoms, preferably ones having 1 to 4 carbon atoms. The lower alkanoyl group means alkanoyl groups having 2 to 6 carbon atoms, preferably ones having 2 to 4 carbon atoms.

The alkyl groups having 1 to 4 carbon atoms are methyl, ethyl, n-propyl, isopropyl, n-butyl, isobutyl, sec-butyl, tert-butyl, etc., and the alkanoyl groups having 2 to 4 carbon atoms are acetyl, propionyl, butyryl, isobutyryl, etc., and the alkylene groups having 3 to 6 carbon are trimethylene group, tetramethylene group, pentamethylene group, hexamethylene group, etc.

The present invention is illustrated in more detail by the following Examples, but should not be construed to be limited thereto.

EXAMPLE 1

(1) 2-n-Propyl-5-acetyl-3-[2'-(1H-tetrazol-5-yl)biphenyl-4-yl]methyl-4,5,6,7-tetrahydroimidazo[4,5-c]pyridine-4-carboxylic acid methyl ester ½ fumarate (300 g) is suspended in a mixture of chloroform (2 liters) and water (1 liter), and the mixture is neutralized with sodium hydrogen carbonate (50 g) to give 2-n-propyl-5-acetyl-3-[2'-(1H-tetrazol-5-yl)biphenyl-4-yl]methyl-4,5,6,7-tetrahydroimidazo[4,5-c]pyridine-4-carboxylic acid methyl ester (270 g).

This product (270 g) is dissolved in chloroform (1.5 liter), and thereto are added triethylamine (65 g) and trityl chloride (158 g), and the mixture is stirred at room temperature overnight. The reaction solution is washed, dried, and evaporated to remove the solvent. The residue is recrystallized from a mixture of ethanol-ether to give 2-n-propyl-5-acetyl-3-[2'-(1-trityl-1H-tetrazol-5-yl)biphenyl-4-yl]methyl-4,5,6,7-tetrahydroimidazo[4,5-c]pyridine-4-carboxylic acid methyl ester (325.8 g).

M.p. 188°–189° C. (decomposed) FAB-MS (m/z): 742 (M+H), 243 (base) NMR (CDCl$_3$) δ: 0.85 and 0.96 (both, t, J=7.3, 3H), 1.73 and 2.20 (both, s, 3H)

(2) The above compound (318 g) is suspended in a mixture of ethanol (2 liters) and tetrahydrofuran (200 ml), and thereto is added a solution of sodium hydroxide (20.0 g) in water (20 ml), and the mixture is stirred at room temperature overnight. The mixture is evaporated to remove the solvent, and thereto is added chloroform (2 liters). The mixture is washed, dried, and evaporated to remove the solvent. The residue is triturated with ether to give 2-n-propyl-5-acetyl-3-[2'-(1-trityl-1H-tetrazol-5-yl)biphenyl-4-yl]methyl-4,5,6,7-tetrahydroimidazo [4,5-c]pyridine-4-carboxylic acid (319 g).

FAB-MS (m/z): 728 (M+1), 243 (base) NMR (DMSO-d$_6$) δ: 0.69 and 0.79 (both, t, J=7.4, 3H), 1.56 and 2.02 (both, s, 3H)

(3) The above compound (2.92 g) is dissolved in dimethylformamide (30 ml), and thereto is added potassium carbonate (0.83 g). The mixture is cooled with ice, and thereto is added dropwise a solution of 3-pentyloxycarbonyloxymethyl chloride (0.87 g) in dimethylformamide (5 ml). After addition, the mixture is warmed to room temperature, and stirred at room temperature overnight. To the mixture is added ethyl acetate, and the mixture is washed, dried, and evaporated to remove the solvent. The residue is purified by silica gel column chromatography (solvent; n-hexane:ethyl acetate=1:1) to give 2-n-propyl-5-acetyl-3-[2'-(1-trityl-1H-tetrazol-5-yl)biphenyl-4-yl]methyl-4,5,6,7-tetrahydroimidazo-[4,5-c]pyridine-4-carboxylic acid 3-pentyloxycarbonyloxymethyl ester (2.95 g) as a caramel.

FAB-MS (m/z): 872 (M+H), 243 (base) NMR (CDCl$_3$) δ: 4.60 (1H, quint), 5.18 (2H, ABq), 5.61 (2H, ABq)

(4) To the above product (2.92 g) is added 85% formic acid (20 ml) under ice-cooling, and the mixture is warmed to room temperature, and stirred for one hour. The reaction solution is diluted with ice-water, and the insoluble materials are removed by filtration, and washed. The filtrate is neutralized with saturated aqueous sodium hydrogen carbonate solution under ice-cooling, and extracted with chloroform. The extract is washed, dried, and evaporated to remove the solvent. The residue is purified by silica gel column chromatography (solvent; chloroform:methanol=50:1) to give 2-n-propyl-5-acetyl-3-[2'-(1H-tetrazol-5-yl)biphenyl-4-yl]methyl-4,5,6,7-tetrahydroimidazo[4,5-c]pyridine-4-carboxylic acid 3-pentyloxycarbonyloxymethyl ester (2.09 g) as a caramel. This product (0.50 g) is dissolved in ethanol, and thereto is added a 27% solution of hydrogen chloride in ethanol, and the mixture is evaporated to remove the solvent. The residue is recrystallized from a mixture of ethanol-ether to give 2-n-propyl-5-acetyl-3-[2'-(1H-tetrazol-5-yl)biphenyl-4-yl]methyl-4,5,6,7-tetrahydroimidazo[4,5-c]pyridine-4-carboxylic acid 3-pentyloxycarbonyloxymethyl ester hydrochloride (0.31 g).

M.p.: 198°–200° C. (decomposed) FAB-MS (m/z): 630 (M+H), 207 (base) NMR (DMSO-d$_6$) δ: 4.54 (1H, quint)

EXAMPLES 2–3

(1) 2-n-Propyl-5-acetyl-3-[2'-(1-trityl-1H-tetrazol-5-yl)biphenyl-4-yl]methyl-4,5,6,7-tetrahydroimidazo[4,5-c]pyridine-4-carboxylic acid obtained in Example 1-(2) and the corresponding starting compound [III] are treated in the same manner as in Example 1-(3) to give the compounds as listed in Table 1.

TABLE 1

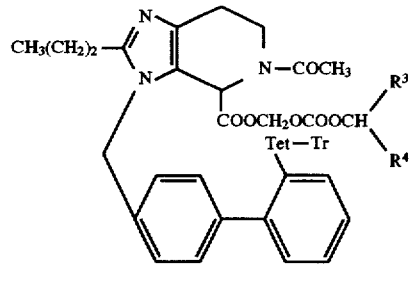

(Tet — Tr: 1-Trityl-1H-tetrazol-5-yl group)

| Example No. | $R^3$ | $R^4$ | FAB-MS (m/z) | NMR(CDCL$_3$)δ |
|---|---|---|---|---|
| 2-(1) | —CH$_3$ | —CH$_3$ | 844 (M + H) 244 (base) | 0.85 (3H, t) 5.18 (2H, ABq) 5.57 (2H, ABq) |
| 3-(1) | —(CH$_2$)$_5$— | | 884 (M + H) | 0.83 (3H, t) |

TABLE 1-continued (Structure: CH₃(CH₂)₂-imidazo[4,5-c]pyridine with N—COCH₃, COOCH₂OOCCH(R³)(R⁴), biphenyl with Tet—Tr substituent)

(Tet—Tr: 1-Trityl-1H-tetrazol-5-yl group)

| Example No. | R³ | R⁴ | FAB-MS (m/z) | NMR(CDCL₃)δ |
|---|---|---|---|---|
|  |  |  | 243 (base) | 5.18 (2H, ABq) |
|  |  |  |  | 5.58 (2H, ABq) |

(2) The above products are treated in the same manner as in Example 1-(4) to give the compounds as listed in Table 2.

TABLE 2

(Structure: CH₃(CH₂)₂-imidazo[4,5-c]pyridine with N—COCH₃, COOCH₂OOCCH(R³)(R⁴), biphenyl with Tet group · HCl)

(Tet: 1H-Tetrazol-5-yl group)

| Ex. No. | R³ | R⁴ | M.p. (°C.) | FAB-MS (m/z) | NMR (DMSO-d₆) δ |
|---|---|---|---|---|---|
| 2-(2) | —CH₃ | —CH₃ | 165–169 (decomp.) | 602 (M + H, base) | 0.83 (3H, t) 1.23 (6H, d) |
| 3-(2) | —(CH₂)₅— |  | 188–189 (decomp.) | 642 (M + H, base) | 0.83 (3H, t) |

PREPARATION 1

A mixture of methyl chloroformate (25.0 g), sulfuryl chloride (35.7 g) and α,α'-azobis(isobutyronitrile) (100 mg) is refluxed for 8 hours. After cooling, the reaction mixture is diluted with hexane (150 ml) and 3-pentanol (24.0 g) is added thereto. Pyridine (42.0 g) is added dropwise to the mixture for 20 minutes under ice-cooling and stirring. After the mixture is stirred at room temperature overnight, hexane (200 ml) is added thereto. The reaction mixture is washed with water, dried, filtered and evaporated to remove the solvent. The residue is distilled under reduced pressure to give 3-pentyloxycarbonyloxymethyl chloride (26.3 g).

B.p. 102°–105° C. (34 mmHg)

PREPARATIONS 2–3

Methyl chloroformate, sulfuryl chloride and the corresponding alcohol compound [X] are treated in the same manner as in Preparation 1 to give the compounds as listed in Table 3.

TABLE 3

Cl—CH₂OCOOCH(R³)(R⁴)

| Preparation No. | R³ | R⁴ | B.p. |
|---|---|---|---|
| 2 | —CH₃ | —CH₃ | 65° C. (20 mmHg) |
| 3 | —(CH₂)₅— |  | 107–109° C. (9 mmHg) |

EFFECTS OF THE INVENTION

The imidazopyridine derivatives [I] of the present invention and a pharmaceutically acceptable salt thereof show more excellent angiotensin II antagonistic activities than the conventional imidazopyridine derivatives and are useful for the prophylaxis or treatment of hypertension in warm-blooded animals including human beings. For example, when the hypotensive activity thereof was examined by using spontaneously hypertension rats, one of the desired compounds of the present invention, 2-n-propyl-5-acetyl-3-[2'-(1H-tetrazol-5-yl)biphenyl-4-yl]methyl-4,5,6,7-tetrahydroimidazo[4,5-c]pyridine-4-carboxylic acid (3-pentyl)oxycarbonyloxymethyl ester showed the hypotensive activity three times as strong as that of the corresponding free carboxylic acid compound or the corresponding methyl ester thereof.

Moreover, the compounds [I] of the present invention and a pharmaceutically acceptable salt thereof can be well absorbed at the digestive organs and thereafter rapidly become the activate form, so that the concentration in the blood thereof is high. Thus, the compounds [I] of the present invention and a pharmaceutically acceptable salt thereof can be used as a medicament safely and properly.

Besides, the compounds [I] of the present invention and a pharmaceutically acceptable salt thereof (especially a hydrochloride thereof) are excellent in crystallizability so that they can be isolated with high purity. The compounds [I] of the present invention and a pharmaceutically acceptable salt thereof are stable against temperature, light, humidity, etc., so that they can be advantageously used in the prophylaxis or treatment of hypertension.

Further, the compounds [I] of the present invention and a pharmaceutically acceptable salt thereof are low toxic, and hence, they show high safety as a medicament.

What is claimed is:

1. 2-n-Propyl-5-acetyl-3-[2'-(1H-tetrazol-5-yl)biphenyl-4-yl]methyl-4,5,6,7-tetrahydroimidazo[4,5-c]pyridine-4-carboxylic acid (3-pentyl)oxycarbonyloxymethyl ester, or a pharmaceutically acceptable salt thereof.

2. 2-n-Propyl-5-acetyl-3-[2'-(1H-tetrazol-5-yl)biphenyl-4-yl]methyl-4,5,6,7-tetrahydroimidazo[4,5-c]pyridine-4-carboxylic acid cyclohexyloxycarbonyloxymethyl ester, or a pharmaceutically acceptable salt thereof.

3. The compound according to claim 1 or 2, wherein the pharmaceutically acceptable salt is a hydrochloride.

4. A pharmaceutical composition which comprises a therapeutically effective amount of the compound as set forth in claim 1 in admixture with a conventional pharmaceutically acceptable carrier or diluent.

5. A method for the prophylaxis or treatment of hypertension in a warm-blooded animal which comprises administering a therapeutically effective amount of the compound as set forth in claim 1 to a subject suffered from hypertension.

6. A method for the prophylaxis or treatment of hypertension in a warm-blooded animal which comprises administering a therapeutically effective amount of the compound as set forth in claim 2 to a subject suffered from hypertension.

7. A pharmaceutical composition which comprises a therapeutically effective amount of the compound as set forth in claim 2 in admixture with a conventional pharmaceutically acceptable carrier or diluent.

* * * * *